US007005137B1

(12) United States Patent
Hossainy et al.

(10) Patent No.: US 7,005,137 B1
(45) Date of Patent: Feb. 28, 2006

(54) COATING FOR IMPLANTABLE MEDICAL DEVICES

(75) Inventors: Syed F. A. Hossainy, Fremont, CA (US); Stephen D. Pacetti, San Jose, CA (US)

(73) Assignee: Advanceed Cardiovascular Systems, Inc., Santa Clara, CA (US)

( * ) Notice: Subject to any disclaimer, the term of this patent is extended or adjusted under 35 U.S.C. 154(b) by 357 days.

(21) Appl. No.: 10/176,510

(22) Filed: Jun. 21, 2002

(51) Int. Cl.
  *A61F 2/02* (2006.01)
(52) U.S. Cl. .................................................. 424/423
(58) Field of Classification Search ................. 424/423
  See application file for complete search history.

(56) References Cited

U.S. PATENT DOCUMENTS

| | | |
|---|---|---|
| 2,968,649 A | 1/1961 | Pailthorp et al. |
| 3,051,677 A | 8/1962 | Rexford |
| 3,178,399 A | 4/1965 | Lo |
| 3,324,069 A | 6/1967 | Koblitz et al. |
| 3,779,805 A | 12/1973 | Alsberg |
| 3,856,827 A | 12/1974 | Cavitt |
| 4,076,929 A | 2/1978 | Dohany |
| 4,197,380 A | 4/1980 | Chao et al. |
| 4,304,010 A | 12/1981 | Mano |
| 4,346,710 A | 8/1982 | Thanawalla et al. |
| 4,353,960 A | 10/1982 | Endo et al. |
| 4,399,264 A | 8/1983 | Squire |
| 4,413,359 A | 11/1983 | Akiyama et al. |
| 4,423,183 A | 12/1983 | Close |
| 4,485,250 A | 11/1984 | Squire |
| 4,530,569 A | 7/1985 | Squire |
| 4,564,013 A | 1/1986 | Lilenfeld et al. |
| 4,569,978 A | 2/1986 | Barber |
| 4,632,842 A | 12/1986 | Karwoski et al. |
| 4,636,346 A | 1/1987 | Gold et al. |
| 4,718,907 A | 1/1988 | Karwoski et al. |
| 4,733,665 A | 3/1988 | Palmaz |
| 4,749,585 A | 6/1988 | Greco et al. |
| 4,754,009 A | 6/1988 | Squire |
| 4,770,939 A | 9/1988 | Sietsess et al. |
| 4,800,882 A | 1/1989 | Gianturco |
| 4,871,357 A | 10/1989 | Hsu et al. |
| 4,876,109 A | 10/1989 | Mayer et al. |
| 4,886,062 A | 12/1989 | Wiktor |
| 4,897,457 A | 1/1990 | Nakamura et al. |
| 4,908,404 A | 3/1990 | Benedict et al. |
| 4,910,276 A | 3/1990 | Nakamura et al. |
| 4,931,287 A | 6/1990 | Bae et al. .................. 424/484 |
| 4,935,477 A | 6/1990 | Squire |
| 4,948,851 A | 8/1990 | Squire |
| 4,973,142 A | 11/1990 | Squire |
| 4,975,505 A | 12/1990 | Squire |
| 4,977,008 A | 12/1990 | Squire |
| 4,977,025 A | 12/1990 | Squire |
| 4,977,026 A | 12/1990 | Squire |
| 4,977,297 A | 12/1990 | Squire |
| 4,977,901 A | 12/1990 | Ofstead .................. 128/772 |
| 4,982,056 A | 1/1991 | Squire |
| 4,985,308 A | 1/1991 | Squire |
| 4,999,248 A | 3/1991 | Squire |
| 5,000,547 A | 3/1991 | Squire |
| 5,006,382 A | 4/1991 | Squire |
| 5,030,394 A | 7/1991 | Sietses et al. |
| 5,047,020 A | 9/1991 | Hsu |
| 5,051,114 A | 9/1991 | Nemser et al. |
| 5,051,978 A | 9/1991 | Mayer et al. |
| 5,053,048 A | 10/1991 | Pinchuk |
| 5,076,659 A | 12/1991 | Bekiarian et al. |
| 5,093,427 A | 3/1992 | Barber |
| 5,107,852 A | 4/1992 | Davidson et al. |
| 5,110,645 A | 5/1992 | Matsumoto et al. |
| 5,112,457 A | 5/1992 | Marchant .................. 204/165 |
| 5,176,972 A | 1/1993 | Bloom et al. |
| 5,185,408 A | 2/1993 | Tang et al. |
| 5,246,451 A | 9/1993 | Trescony et al. |
| 5,276,121 A | 1/1994 | Resnick |
| 5,296,283 A | 3/1994 | Froggatt |
| 5,302,385 A * | 4/1994 | Khan et al. .................. 424/486 |
| 5,308,685 A | 5/1994 | Froggatt |
| 5,310,838 A | 5/1994 | Hung et al. |
| 5,324,889 A | 6/1994 | Resnick |
| 5,326,839 A | 7/1994 | Resnick |
| 5,328,471 A | 7/1994 | Slepian .................. 604/101 |
| 5,336,518 A | 8/1994 | Narayanan et al. |
| 5,338,608 A | 8/1994 | Resnick |
| 5,342,348 A | 8/1994 | Kaplan |
| 5,353,368 A | 10/1994 | Resnick |
| 5,354,910 A | 10/1994 | Hung et al. |
| 5,368,566 A | 11/1994 | Crocker |
| 5,380,299 A | 1/1995 | Fearnot et al. |
| 5,383,853 A | 1/1995 | Jung et al. |
| 5,383,928 A | 1/1995 | Scott et al. |
| 5,395,311 A | 3/1995 | Andrews |
| 5,403,341 A | 4/1995 | Solar |
| 5,408,020 A | 4/1995 | Hung et al. |
| 5,417,969 A | 5/1995 | Hsu et al. |
| 5,443,458 A | 8/1995 | Eury |
| 5,447,724 A | 9/1995 | Helmus et al. |

(Continued)

FOREIGN PATENT DOCUMENTS

DE         19723723 A1     12/1998

(Continued)

OTHER PUBLICATIONS

U.S. Appl. No. 09/966,036, filed Sep. 28, 2001, Happ.

(Continued)

*Primary Examiner*—Carlos A. Azpuru
(74) *Attorney, Agent, or Firm*—Squire, Sanders & Dempsey, L.L.P.

(57) ABSTRACT

A coating for an implantable medical device, such as a stent, is disclosed. The coating comprising a block copolymer obtained by a polymerization reaction of at least two reagents. A method for forming the coating is also disclosed.

40 Claims, No Drawings

U.S. PATENT DOCUMENTS

| | | | |
|---|---|---|---|
| 5,455,040 A | 10/1995 | Marchant | 424/426 |
| 5,464,650 A | 11/1995 | Berg et al. | 427/2.3 |
| 5,545,208 A | 8/1996 | Wolff et al. | |
| 5,560,463 A | 10/1996 | Link et al. | |
| 5,562,734 A | 10/1996 | King | |
| 5,569,463 A | 10/1996 | Helmus et al. | |
| 5,575,818 A | 11/1996 | Pinchuk | |
| 5,578,073 A | 11/1996 | Haimovich et al. | 623/1 |
| 5,584,877 A | 12/1996 | Miyake | 623/1 |
| 5,591,224 A | 1/1997 | Schwartz et al. | |
| 5,604,283 A | 2/1997 | Wada et al. | |
| 5,605,696 A | 2/1997 | Eury et al. | 424/423 |
| 5,616,608 A | 4/1997 | Kinsella et al. | |
| 5,628,728 A | 5/1997 | Tachibana et al. | |
| 5,632,771 A | 5/1997 | Boatman et al. | |
| 5,632,776 A | 5/1997 | Kurumatani et al. | |
| 5,632,840 A | 5/1997 | Campbell | |
| 5,635,201 A | 6/1997 | Fabo | |
| 5,667,767 A | 9/1997 | Greff et al. | 424/9.411 |
| 5,670,558 A | 9/1997 | Onishi et al. | 523/112 |
| 5,679,400 A | 10/1997 | Tuch | |
| 5,684,061 A | 11/1997 | Ohnishi et al. | |
| 5,691,311 A | 11/1997 | Maraganore et al. | |
| 5,697,967 A | 12/1997 | Dinh et al. | |
| 5,700,286 A | 12/1997 | Tartaglia et al. | 623/1 |
| 5,713,949 A | 2/1998 | Jayaraman | |
| 5,716,981 A | 2/1998 | Hunter et al. | 514/449 |
| 5,750,234 A | 5/1998 | Johnson et al. | |
| 5,758,205 A | 5/1998 | Hara et al. | |
| 5,759,205 A | 6/1998 | Valentini | 623/16 |
| 5,760,118 A | 6/1998 | Sinclair et al. | |
| 5,776,184 A | 7/1998 | Tuch | |
| 5,804,318 A | 9/1998 | Pinchuk et al. | |
| 5,820,917 A | 10/1998 | Tuch | |
| 5,824,048 A | 10/1998 | Tuch | |
| 5,824,049 A | 10/1998 | Ragheb et al. | 623/1 |
| 5,827,587 A | 10/1998 | Fukushi | |
| 5,830,178 A | 11/1998 | Jones et al. | 604/49 |
| 5,837,008 A | 11/1998 | Berg et al. | |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,858,990 A | 1/1999 | Walsh | 514/44 |
| 5,860,963 A | 1/1999 | Azam et al. | |
| 5,861,168 A | 1/1999 | Cooke et al. | |
| 5,865,814 A | 2/1999 | Tuch | 604/265 |
| 5,869,127 A | 2/1999 | Zhong | |
| 5,873,904 A | 2/1999 | Ragheb et al. | 623/1 |
| 5,874,165 A | 2/1999 | Drumheller | |
| 5,879,697 A | 3/1999 | Ding et al. | |
| 5,897,911 A | 4/1999 | Loeffler | |
| 5,900,425 A | 5/1999 | Kanikanti et al. | |
| 5,911,704 A | 6/1999 | Humes | |
| 5,921,933 A | 7/1999 | Sarkis et al. | |
| 5,922,393 A | 7/1999 | Jayaraman | |
| 5,928,279 A | 7/1999 | Shannon et al. | |
| 5,932,299 A | 8/1999 | Katoot | |
| 5,945,115 A | 8/1999 | Dunn et al. | |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,015,541 A | 1/2000 | Greff et al. | 424/1.25 |
| 6,033,724 A | 3/2000 | Molitor | |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,534 A | 5/2000 | Ronan et al. | |
| 6,080,488 A | 6/2000 | Hostettler et al. | 428/423.3 |
| 6,090,134 A | 7/2000 | Tu et al. | |
| 6,096,070 A | 8/2000 | Ragheb et al. | 623/1 |
| 6,096,396 A | 8/2000 | Patton et al. | |
| 6,096,798 A | 8/2000 | Luthra et al. | |
| 6,096,809 A * | 8/2000 | Lorcks et al. | 524/47 |
| 6,099,562 A | 8/2000 | Ding et al. | 623/1.46 |
| 6,099,563 A | 8/2000 | Zhong | |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,124,045 A | 9/2000 | Soda et al. | |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,179,817 B1 | 1/2001 | Zhong | |
| 6,197,051 B1 | 3/2001 | Zhong | |
| 6,203,551 B1 | 3/2001 | Wu | 606/108 |
| 6,214,901 B1 | 4/2001 | Chudzik et al. | 523/113 |
| 6,224,894 B1 | 5/2001 | Jamiolkowski et al. | 424/426 |
| 6,231,590 B1 | 5/2001 | Slaikeu et al. | 606/200 |
| 6,242,041 B1 | 6/2001 | Katoot et al. | 427/2.24 |
| 6,254,632 B1 | 7/2001 | Wu et al. | 623/1.15 |
| 6,258,121 B1 | 7/2001 | Yang et al. | 623/1.46 |
| 6,262,034 B1 | 7/2001 | Mathiowitz et al. | 514/44 |
| 6,273,913 B1 | 8/2001 | Wright et al. | 623/1.42 |
| 6,299,604 B1 | 10/2001 | Ragheb et al. | |
| 6,319,520 B1 | 11/2001 | Wuthrich et al. | 424/482 |
| 6,344,035 B1 | 2/2002 | Chudzik et al. | 604/265 |
| 6,362,271 B1 | 3/2002 | Lin et al. | |
| 6,408,878 B1 | 6/2002 | Unger et al. | |
| 6,410,612 B1 | 6/2002 | Hatanaka | |
| 6,464,683 B1 | 10/2002 | Samuelson et al. | |
| 6,503,556 B1 | 1/2003 | Harish et al. | |
| 6,545,097 B1 * | 4/2003 | Pinchuk et al. | 525/240 |
| 6,551,708 B1 | 4/2003 | Tsuda et al. | |
| 6,716,444 B1 | 4/2004 | Castro et al. | |
| 6,746,773 B1 | 6/2004 | Llanos et al. | |
| 2001/0014717 A1 | 8/2001 | Hossainy et al. | |
| 2001/0029351 A1 | 10/2001 | Falotico et al. | |
| 2002/0051730 A1 | 5/2002 | Bodnar et al. | |
| 2002/0090389 A1 | 7/2002 | Humes et al. | |
| 2002/0094440 A1 | 7/2002 | Llanos et al. | 428/421 |
| 2002/0099438 A1 | 7/2002 | Furst | |
| 2002/0111590 A1 | 8/2002 | Davila et al. | 604/265 |
| 2002/0122877 A1 | 9/2002 | Harish et al. | |
| 2002/0123017 A1 | 9/2002 | Pacetti et al. | |
| 2002/0133183 A1 | 9/2002 | Lentz et al. | |
| 2002/0143386 A1 | 10/2002 | Davila et al. | |
| 2002/0165608 A1 | 11/2002 | Llanos et al. | |
| 2002/0188037 A1 | 12/2002 | Chudzik et al. | |
| 2003/0004563 A1 | 1/2003 | Jackson et al. | |
| 2003/0031780 A1 | 2/2003 | Chudzik et al. | |
| 2003/0039689 A1 | 2/2003 | Chen et al. | |
| 2003/0060877 A1 | 3/2003 | Falotico et al. | |
| 2003/0065346 A1 | 4/2003 | Evens et al. | |
| 2003/0065377 A1 | 4/2003 | Davila et al. | |
| 2003/0073961 A1 | 4/2003 | Happ | |
| 2003/0077312 A1 | 4/2003 | Schmulewicz et al. | |
| 2004/0102758 A1 | 5/2004 | Davila et al. | |

FOREIGN PATENT DOCUMENTS

| | | |
|---|---|---|
| EP | 0568310 A1 | 11/1993 |
| EP | 0623354 A1 | 11/1994 |
| EP | 0633032 A1 | 1/1995 |
| EP | 0 665 023 | 8/1995 |
| EP | 0747069 A2 | 12/1996 |
| EP | 0815803 A1 | 1/1998 |
| EP | 0893108 A2 | 1/1999 |
| EP | 0950385 A2 | 10/1999 |
| EP | 0950386 A2 | 10/1999 |

| | | |
|---|---|---|
| EP | 0 970 711 | 1/2000 |
| EP | 0968688 A1 | 1/2000 |
| EP | 0997115 A2 | 5/2000 |
| EP | 1 023 879 | 8/2000 |
| EP | 1 192 957 | 4/2002 |
| WO | WO 92/05695 | 4/1992 |
| WO | WO 92/18320 | 10/1992 |
| WO | WO 94/02185 | 2/1994 |
| WO | WO 96/21404 | 7/1996 |
| WO | WO 97/41164 | 11/1997 |
| WO | WO 98/08463 | 3/1998 |
| WO | WO 98/13405 | 4/1998 |
| WO | WO 98/36784 | 8/1998 |
| WO | WO 98/58680 | 12/1998 |
| WO | WO 99/32051 | 7/1999 |
| WO | WO 99/55396 | 11/1999 |
| WO | WO 00/02599 | 1/2000 |
| WO | WO 00/12147 | 3/2000 |
| WO | WO 00/27455 | 5/2000 |
| WO | WO 00/29043 | 5/2000 |
| WO | WO 00/32255 | 6/2000 |
| WO | WO 00/38754 | 7/2000 |
| WO | WO 00/41738 | 7/2000 |
| WO | WO 00/64506 | 11/2000 |
| WO | WO 01/01890 | 1/2001 |
| WO | WO 01/30403 A1 | 5/2001 |
| WO | WO 01/49340 | 7/2001 |
| WO | WO 01/87342 A2 | 11/2001 |
| WO | WO 01/87368 | 11/2001 |
| WO | WO 01/87372 | 11/2001 |
| WO | WO 01/87376 A1 | 11/2001 |
| WO | WO 02/24249 | 3/2002 |
| WO | WO 02/26139 A1 | 4/2002 |
| WO | WO 02/26271 A | 4/2002 |
| WO | WO 02/26281 A1 | 4/2002 |
| WO | WO 02/47731 | 6/2002 |
| WO | WO 02/47732 | 6/2002 |
| WO | WO 03/022324 | 3/2003 |

OTHER PUBLICATIONS

U.S. Appl. No. 10/176,504, filed Jun. 21, 2002, Roorda et al.
U.S. Appl. No. 10/177,117, filed Jun. 21, 2002, Hossainy.
U.S. Appl. No. 10/177,154, filed Jun. 21, 2002, Hossainy et al.
U.S. Appl. No. 10/198,912, filed Jul. 19, 2002, Ding et al.
U.S. Appl. No. 10/251,111, filed Sep. 19, 2002, Hossainy et al.
U.S. Appl. No. 10/320,899, filed Dec. 16, 2002, Shah et al.
U.S. Appl. No. 10/376,348, filed Feb. 26, 2003, Ding et al.
U.S. Appl. No. 10/428,691, filed May 1, 2003, Pacetti.
U.S. Appl. No. 10/931,927, filed Aug. 31, 2004, Pacetti.
Anonymous, *Rolling Therapeutic Agent Loading Device for Therapeutic Agent Delivery of Coated Stent*, Research Disclosure, Publ., Hampshire, GB, No. 434, p. 975 (2000).
Arnold et al., *Effects of environment on the creep properties of a poly (ethylmethacrylate) based bone cement* J. Mater. Sci: Mater. In Med., vol. 12, pp. 707-717 (2001).
Bellex International, *CYTOP®, Amorphous Fluorocarbon Polymer*, 1 page (no date).
Bellex International, *CYTOP ®*, http://www.bellexinternational.com/cytop.htm, printed Mar. 30, 2001, 1 page.
Cifková et al., *Irritation effects of residual products derived from p(HEMA) gels*, Biomaterials, vol. 9, (Jul. 1998), pp. 372-375.
Dalsin et al., *DOPA: A New Anchor for PEGylation of Biomaterial Surfaces*, Soc. For Biomaterials 28th Annual Meeting Transactions, pp. 40 (2002).

Deb et al., *Effect of crosslinking agents on poly (ethylmethacrylate) bone cements*, J. of Mater.Sci: Mater. In Med., vol. 8, pp. 829-833 (1997).
Del Guerra et al., *In vitro biocompatibility of fluorinated polyurethanes*, J. Mater. Sci. in Med., vol. 5, pp. 452-456 (1994).
DuPont, *Teflon AF 1601S amorphous fluoropolymer solutions*, product information, 2 pages (1998).
DuPont, *Processing of Teflon® AF*, Teflon Amorphous Fluoropolymer, http://www.dupont.com/teflon/af/processing.html, printed Mar. 30, 2001, 1 page.
DuPont, *High-Performance/Potential Applications*, Teflon Amorphous Fluoropolymer, http://www.dupont.com/teflon/af/potapps.html, printed Mar. 30, 2001, 3 pages.
DuPont, *Performance Comparison of Teflon AF*, Teflon Amorphous Fluoropolymer, http://www.dupont.com/teflon/af/performance.html, printed Mar. 30, 2001, 3 pages.
DuPont, *Unique Properties of Teflon® AF*, Teflon Amorphous Fluoropolymer, http://www.dupont.com/teflon/af/unique.html, printed Mar. 30, 2001, 3 pages.
DuPont, *Teflon® AF: A New Generation of High-Performance Fluoropolymer Resins*, http://www.dupont.com/teflon/af/index.html, printed Mar. 30, 2001, 1 page.
DuPont, *Teflon® Protects Superconductors Against Acid*, Teflon Amorphous Fluoropolymer, http://www.dupont.com/teflon/af/superconductor.html, printed Sep. 21, 2004, 2 pages.
DuPont, *Available Grades of DuPont Teflon® AF*, Teflon Amorphous Fluoropolymer, http://www.dupont.com/teflon/af/grades.html, printed Sep. 21, 2004, 2 pages.
DuPont, *Teflon® AF amorphous fluoropolymers*, Product Information, 6 pages (1998).
DuPont, Sales Notice, Teflon Amorphous Fluoropolymer, http://www.dupont.com/teflon/af/patent.html, printed Sep. 21, 2004, 2 pages.
Fine et al., *Improved nerve regeneration through piezoelectric vinylidenefluoride- trifluoroethylene copolymer guidance channels*, Biomaterials, vol. 12, Oct., pp. 775-780 (1991).
Fischell, *Polymer Coatings for Stents*, Circulation, 94:1494-95 (1996).
Gullickson, *Reference Data Sheet on Common Chlorinated Solvents*, http://www.mcs.net/~hutter/tee/chlorina.html, printed Mar. 30, 2001, 5 pages.
Gunn et al., *Stent coatings and local drug delivery*, Eur. Heart J., vol. 20, issue 23, pp. 1693-1700 (1999).
Harper et al., *Fatigue Characteristics of Polyethylmethacrylate Based Bone Cement Reinforced with Silane Coupled Hydroxyapatite*, Fifth World Biomaterials Congress, May 29-Jun. 2, 1996, Toronto, Canada, Abstract 351, 3 pgs.
Harper et al., *Mechanical properties of hydroxyapatite reinforced poly (ethyl methacrylate) bone cement after immersion in a physiological solution: influence of a silane coupling agent*, J. Mater. Sci.: Mater. In Med., vol. 11, pp. 491-497 (2000).
Kruft et al., *Studies on radio-opaque polymeric biomaterials with potential applications to endovascular prostheses*, Biomaterials, vol. 17, No. 18, pp. 1803-1812 (1996).
Lambert et al., *Localized Arterial Wall Drug Delivery From a Polymer-Coated Removable Metallic Stent*, Circulation, vol. 90, No. 2, pp. 1003-1011 (1994).
Laroche et al., *Polyvinylidene fluoride (PVDF) as a biomaterial: From polymeric raw material to monofilament*

*vascular suture*, J. of Biomedical Mat. Research, vol. 29, pp. 1525-1536 (1995).

Lin et al., *Fluropolymer Alloys Performance Optimization of PVDF Alloys*, Fluropolymers 2 Properties, edited by Hougham et al., Plenum Publishers N.Y. pp. 121-136 (1999).

Lin et al., *Surface characterization and platelet adhesion studies on fluorocarbons prepared by plasma-induced graft polymerization*, J. Biomater Sci. Polymer Edn., vol. 11, No. 7, pp. 701-714 (2000).

Luthra, Biointeractions Ltd (BIL), http://www.biomateria.com/biointeractions.html, printed Sep. 21, 2004, 3 pages.

3M, *Specialty Fluids 3M™ Fluorinert™ Liquids, Typical Properties*, http://www.3m.com/market/industrial/fluids/fluoprop.html, printed Mar. 30, 2001, 3 pages.

Materials Engineering, *Applications in Design/Manufacturing/R&D*, Materials Selector 1993, Penton Publishing (1992) 6 pgs.

Medtronic, Trillium Affinity NT, Oxygenator, Product Information, 6 pages (2000).

NCMS SOLV-DB, *Query Results for: CFC*, http://solvdb.ncms.org/CAT01.idc?chemcat=CFC, printed Mar. 30, 2001, 2 pages.

NCMS SOLV-DB, *Query Results for: FC-75 Fluorinert*, http://solvdb.ncms.org/common01.idc, printed Mar. 30, 2001, 2 pages.

Novick et al., *Protein-containing hydrophobic coatings and films*, Biomaterials, vol. 23, No. 2 (2002) pp. 441-448.

Parkell, Inc., *SNAP Powder-Liquid Temporary Crown and Bridge Resin*, http://www.parkell.com/snap.html, printed Oct. 21, 2004, 1 pg.

Parkell, Inc., *Material Safety Data Sheets*, http://www.parkell.com/msds.html, printed Oct. 21, 2004, 2 pgs.

Parkell, Inc., *MSDS No.: S426, VAR, Material Safety Data Sheet*, 2 pgs (2002).

Parkell, Inc., MSDS No.: S441, Material Safety Data Sheet, 2 pgs (2002).

Porté-Durrieu et al., *Surface Treatment of Biomaterials by Gamma and Swift Heavy Ions Grafting*, Nuclear Instruments and Methods in Physics Research, vol. B 151, pp. 404-415 (1999).

Porté-Durrieu et al., *Development of "Heparin-Like" Polymers Using Swift Heavy Ion and Gamma Radiation. I. Preparation and Characterization of the Materials*, Surface Treatment of Biomaterials, pp. 119-127 (2000).

Revell et al., *Experimental Studies of the Biological Response to a New Bone Cement: II Soft Tissue Reactions in the Rat*, Clinical Materials, vol.: 10, pp. 233-238 (1992).

Techspray, Bulk Solvents, http://www.techspray.com/bulksup.htm, printed Sep. 21, 2004, 3 pages.

Techspray, *Flux Remover AMS*, Product Information, http://www.techspray.com/1665info.htm, printed Aug. 28, 2001, 2 pages.

Teomin et al., *Perivascular delivery of heparin for the reduction of smooth muscle cell proliferation after endothelial injury*, J. of Controlled Release, vol. 60, pp. 129-142 (1999).

Topol et al., *Frontiers in Interventional Cardiology*, Circulation, vol. 98, pp. 1802-1820 (1998).

Urban et al., *Why Make Monofilament Sutures Out of Polyvinylidene Fluoride?*, ASAIO J., vol. 40, No. 2, pp 145-156 (1994).

Verweire et al., *Evaluation of fluorinated polymers as coronary stent coating*, J. Mater.Sci: Mater. In Med., vol. 11, No. 4, pp. 207-212 (2000).

Weightman et al., *The Mechanical Properties of Cement and Loosening of the Femoral Component of Hip Replacements*, J. Bone and Joint Surg., vol. 69-B, No. 4, pp. 558-564 (Aug. 1987).

Wholey et al., *Global Experience in Cervical Carotid Artery Stent Placement*, Catherization and Cardiovascular Inteventions, vol. 50, No. 2, pp. 160-167 (2000).

Woo et al., *Phase Behavior of Polycarbonate Blends with Selected Halogenated Polymers*, J. Appl. Polym. Sci., vol. 30, pp. 4243-4249 (1985).

International Search Report for PCT appl. PCT/US03/15347, filed May 14, 2003, date of mailing Sep. 4, 2003, 6 pgs.

International Search Report for PCT appl. PCT/US03/15544, filed May 14, 2003, date of mailing Jan. 23, 2004, 9 pgs.

International Search Report for PCT appl. PCT/US03/28643, filed Sep. 10, 2003, date of mailing Mar. 12, 2003, 10 pgs.

International Search Report for PCT appl. PCT/US03/21170, filed Jul. 2, 2003, date of mailing Oct. 31, 2003, 8 pgs.

U.S. Appl. No. 09/894,293, filed Jun. 27, 2001, Roorda et al.

\* cited by examiner

COATING FOR IMPLANTABLE MEDICAL DEVICES

BACKGROUND OF THE INVENTION

1. Field of the Invention

This invention is directed to coatings for implantable medical devices, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer. Once the stent has been implanted at the treatment site, the therapeutic substance has a sustained release profile from the polymer.

The embodiments of the present invention provide for polymers and combination of polymers for coating stents and other implantable medical devices.

SUMMARY

According to one embodiment of the present invention, a coating for an implantable medical device is provided. The coating comprises a block copolymer obtained by a polymerization reaction of a plurality of reagents. The coating can also include an active agent, such as those used for the treatment of restenosis. The implantable device can be, for example, a stent. In one embodiment of the invention, the reagents for the polymerization comprise an isocyanate-derived compound, for example a product of the reaction between a diisocyanate and a diol, and a hydroxyl-group containing compound, for example, a polyglycol or a polysiloxane. According to another embodiment, the reagents for the polymerization comprise polyesters, such as, for example, poly(alkylene terephthalates), or copolymers of these polyesters with polyglycols, such as, for example, poly(ethylene glycol).

A method of fabricating a medical article, such as a stent is also provided. The method comprises coating an implantable medical device with a polymer composition, wherein the polymer composition comprises a block copolymer obtained by a polymerization reaction of a plurality of reagents. The coating can also include an active agent.

DETAILED DESCRIPTION

The term "block copolymer" is defined as a copolymer containing a linear arrangement of blocks, a block being defined as a portion of a polymer molecule in which the monomeric units have at least one constitutional or configurational feature absent from the adjacent portions. For example, a block copolymer of A and B may be written as . . . -A-A-A-A-B-B-B-B-B- . . . . The blocks need not be linked on the ends, since the individual blocks are usually long enough to be considered polymers in their own right. The polymer can be, accordingly, named poly A-block-poly B. The term copolymer is intended to broadly include two or more types of blocks such as triblocks.

One example of a block copolymer that can be used to fabricate a coating or a layer for a coating for a stent is isocyanate-diol based block copolymer which includes poly (dimethylsiloxane) blocks or poly(alkylene glycol) blocks. Other examples of block copolymers include poly(alkylene terephthalate)-poly(alkylene glycol) copolymers, polyester-poly(alkylene glycol) copolymers, copolymers based on fluorinated and/or perfluorinated olefins and polyolefin-polystyrene copolymers.

The coating can be used as a primer layer, a reservoir layer containing an active agent or a drug, or a topcoat layer for reducing the rate of release of the drug. The block copolymers can be used alone, in combination with, or in mixture with other suitable biocompatible polymers. Poly (ethylene-co-vinyl alcohol) (EVAL) is one example of a polymer than can be employed. EVAL has the general formula $—[CH_2—CH_2]_m-[CH_2—CH(OH)]_n—$. EVAL is a product of hydrolysis of ethylene-vinyl acetate copolymers and may also be a terpolymer including up to 5 molar % of units derived from styrene, propylene and other suitable unsaturated monomers.

Other suitable polymers that can also be used in combination with the block copolymer include poly(vinyl alcohol) (PVA) having the general formula $—[CH_2—CH_2(OH)]_m—$, and a polymer known under the trade name Bionate® manufactured by The Polymer Technology Group Incorporated of Berkeley, Calif. Bionate® is a thermoplastic polycarbonate-urethane elastomer formed as the product of the reaction between a hydroxyl-terminated polycarbonate, an aromatic diisocyanate, and a low molecular-weight glycol used as a chain extender. Representative examples of other polymers include poly(hydroxyvalerate), poly(L-lactic acid), polycaprolactone, poly(lactide-co-glycolide), poly (hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane; poly(amino acids), cyanoacrylates, poly (trimethylene carbonate), poly(iminocarbonate), co-poly (ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, other polycarbonates, polyoxymethylenes, polyimides, polyethers, epoxy resins, other polyurethanes, rayon, rayon-triacetate, cellulose, cellulose acetate, cellulose butyrate, cellulose acetate butyrate, cellophane, cellulose nitrate, cellulose propionate, cellulose ethers, soluble fluorinated polymers and carboxymethyl cellulose.

The embodiments of the present invention are described in connection with a stent, e.g., balloon expandable or self-expandable stents; however, other implantable medical devices can also be coated with the described block copolymers. Examples of such implantable devices include stent-grafts, grafts (e.g., aortic grafts), artificial heart valves, cerebrospinal fluid shunts, pacemaker electrodes, and endocardial leads (e.g., FINELINE and ENDOTAK, available from Guidant Corp. of Santa Clara, Calif.). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

For the reservoir layer, the coating can include an active agent or a drug. The active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, derivatives and analogs thereof (manufactured by Sigma-Aldrich of Milwaukee, Wis.), or COSMEGEN available from Merck & Co. Inc. of Whitehouse Station, N.J. Synonyms of actinomycin D include dactinomycin, actinomycin IV, actinomycin 11, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. Taxol® by Bristol-Myers Squibb Co. of Stamford, Conn.), docetaxel (e.g. Taxotere®, from Aventis S. A. of Frankfurt, Germany) methotrexate, azathioprine, vincristine, vinblastine, fluorouracil, doxorubicin hydrochloride (e.g. Adriamycin® from Pharmacia & Upjohn, of Peapack N.J.), and mitomycin (e.g. Mutamycin® from Bristol-Myers Squibb Co. of Stamford). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax made by Biogen, Inc., of Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co. of Stamford), cilazapril or lisinopril (e.g. Prinivil® and Prinzide® from Merck & Co., Inc. of Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., of Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin, dexamethasone, and functional analogs and structural derivatives thereof.

Embodiments of the present invention are further illustrated by the following examples.

EXAMPLE 1

A composition can be prepared by mixing the following components:
(a) between about 0.1 and about 15% (all % are by mass), for example, about 2.0% of a matrix polymer compound, for example, Bionate® polymer;
(b) between about 0.01 and about 1.5%, for example, between about 0.2 and 1.0% of a block-copolymer;
(c) between about 0.05 and about 1.0%, for example, about 0.7% of an active agent, for example, Everolimus (available from Novartis); and
(d) the balance, a solvent, for example, N,N-dimethylacetamide (DMAC) having the formula $CH_3$—CO—N $(CH_3)_2$.

The typical polycarbonate glycol intermediate used for the synthesis of Bionate®, poly(1,6-hexyl-1,2-ethyl carbonate)diol, PHECD, is the product of the condensation of 1,6-hexanediol with cyclic ethylene carbonate. The polycarbonate macroglycol product of the above-mentioned condensation is then reacted with aromatic isocyanate, 4,4'-methylene-bisphenyl-diisocyanate (MDI), and chain-extended with 1,4-butanediol.

Ingredient (b), the block-copolymer, can be a product of co-polycondensation of an isocyanate-based component and a hydrophobic polymeric component. The isocyanate-based component can be synthesized by reacting a diisocyanate, usually, hexamethylene-1,6-diisocyanate, HMDI, having the formula $O=C=N-(CH_2)_6-N=C=O$, with, for example, a diol, such as, butane-1,4-diol having the formula $HO-(CH_2)_4-OH$.

This adduct is reacted with the hydrophobic polymeric component, for example, polydimethylsiloxane (PDMS), having a general formula $-[O-Si-(CH_3)_2]_n-$, to form the block-copolymer. The block-copolymer has an average molecular weight within a range of between about 8,000 and about 50,000. The increase of the molecular weight will improve the protective and the release rate controlling properties, but its solubility may be impaired. Therefore, the molecular weight can be chosen at about 25,000. In case of spraying, the upper limit amount of the block-copolymer can be about 0.5%, and in case of dipping about 1.5%.

The above-described block-copolymer (HMDI-butanediol-co-PDMS) is also known under the trade name Elasteon® and is manufactured by AorTech Biomaterials Co. of Chatswood, Australia.

In addition to the DMAC, alternative solvents that can be used include N,N-dimethylformamide (DMFA) (H—CON(CH$_3$)$_2$), tetrahydrofuran (THF) (C$_4$H$_8$O), or dimethylsulfoxide (DMSO)((CH$_3$)$_2$C=O).

The final composition can be applied on the stent either by spraying or by dipping. In case of spraying, the upper limit amount of Bionate® can be about 5%, and in case of dipping about 15%.

In the final product, because PDMS is a surface-active hydrophobic polymer, the PDMS portion of the composition blooms to the polymer-air interface, thus controlling the rate of release of the active agent. The isocyanate portion stays below the PDMA portion.

EXAMPLE 2

A composition can be prepared by mixing the following components:
(a) between about 0.1 and about 15%, for example, about 2.0% Bionate®;
(b) between about 0.01 and about 1.5%, for example, between about 0.2 and 1.0% block-copolymer;
(c) between about 0.05 and about 1.0%, for example, about 0.7% active agent, for example, Everolimus; and
(d) the balance, DMAC solvent.

Instead of the Elasteon® copolymer utilized in Example 1, another block-copolymer is used as ingredient (b). The copolymer can comprise an HMDI-butane diol adduct, but instead of PDMS of Example 1, the HMDI-butane diol adduct is co-polycondensed with a polyglycol, typically an alkylene glycol, for instance, polyethylene glycol (PEG) having the general formula $H-[O-CH_2-CH_2]_n-OH$. In this formulation, there is no PDMS, and the PEG portion of the block-copolymer does not bloom to the polymer-air interface, unlike PDMS of Example 1. Instead, the PEG portion migrates to the polymer-water interface, the water being provided by the body fluids surrounding the implantable device. The block copolymer can have an average molecular weight within a range of between about 8,000 and about 50,000, for example, about 25,000.

EXAMPLE 3

A coating can be formed on a stent according to a two-step procedure:

Step 1: a coating is applied on the surface of the device, the coating being made from the following composition:
(a) between about 0.1 and about 15%, for example, about 2.0% Bionate®;
(b) between about 0.05 and about 1.0%, for example, about 0.7% active agent, for example, Everolimus; and
(c) the balance, DMAC solvent.

No block copolymer is used in step 1. Instead, the block copolymer is applied in the second step of the procedure, which is performed following the drying of the coating applied in step 1.

Step 2: a topcoat is applied over the coating of step 1. This topcoat is based on a formulation comprising:
(a) between about 0.1 and about 15%, for example, about 2.0% Bionate®;
(b) between about 0.01 and about 1.5%, for example, between about 0.2 and 1.0% block copolymer; and
(c) the balance, DMAC solvent.

The block-copolymer can be the same as the one described in Example 1 above—namely, HMDI-butanediol-co-PDMS product, such as Elasteon®. The block-copolymer can have an average molecular weight within a range of between about 8,000 and about 50,000, for example, about 25,000. Alternative solvents also include DMFA, THF, or DMSO.

Higher loading limits (e.g., 15% Bionate®, and 1.5% block-copolymer) can be used when the composition is applied by dipping, and the lower loading limits (e.g., 5% and 0.5%, respectively) can be used when the composition is applied by spraying.

EXAMPLE 4

A composition can be prepared by mixing the following components:
(a) between about 0.1 and about 15%, for example, about 2.0% polyester, for example, poly(alkylene terephthalate), such as poly(ethylene terephthalate) (PET) with a general formula $-[O-CH_2-CH_2-O-CO-C_6H_4-O-CO-CH_2-CH_2]_n-$;
(b) between about 0.01 and about 1.5%, for example, between about 0.2 and 1.0% block-copolymer;
(c) between about 0.05 and about 1.0%, for example, about 0.7% active agent, for example, Everolimus; and
(d) the balance, solvent, for example, trifluoroacetic anhydride (TFAA), having the formula $(CF_3-CO)_2O$.

Ingredient (b), the block-copolymer, such as PBT-PEG is a product of co-polycondensation of poly(butylene terephthalate) (PBT), having the general formula $-[O-(CH_2)_4-O-CO-C_6H_4'-O-CO-(CH_2)_4]_n-$ with poly(ethylene glycol) (PEG) having the general formula $-[O-CH_2-CH_2-O-CH_2-CH_2]_n-$. A product of polycondensation of monomeric butylene terephthalate and ethylene glycol is also acceptable and may be used as long as the final block-copolymer is formed with a molecular weight of between about 8,000 and about 50,000, for example, about 25,000.

Higher loading limits (e.g., 15% PET and 1.5% for the block-copolymer) can be used when the composition is applied by dipping, and lower loading limits (e.g., 5% and 0.5% respectively) can be used when the composition is applied by spraying.

EXAMPLE 5

The composition according to this example can be made according to the same formulation as in Example 4 with the following exceptions:
(a) instead of PET in ingredient (a) and instead of PBT in the block-copolymer of ingredient (b), a polymer of L-lactic acid is used (PLLA). This polymer is formed by self-condensation of L-lactic acid having the formula $CH_3$—CH(OH)—COOH. The amount of PLLA in the formulation is the same as that of PET or PBT, respectively.
(b) the solvent can be 1,1,2-thrichloroethylene having the formula CHCl=$CCl_2$. Alternatively, DMSO or methyl chloroform (also known as 1,2,3-trichloroethane), having the formula $CH_3$—$CCl_3$, can be used. The amounts of the solvents used are the same as those of Example 4.

EXAMPLE 6

The composition can be made according to the formulation described in Example 1, except that EVAL is used as a matrix polymer, instead of Bionate®.

EXAMPLE 7

The composition can be made according to the formulation described in Example 1, except that in the soft portion of the block co-polymer a long-chained glycol is used instead of PDMS. The long-chained glycol has the general formula HO—$(CH_2)_n$—OH, where "n" is an integer having a value of at least 18.

EXAMPLE 8

A coating can be formed on a stent according to a two-step procedure:

Step 1: a coating is applied on the device to form a drug-polymer layer, the coating being made from the following composition:
(a) between about 0.1 and about 15%, for example, about 2.0% EVAL;
(b) between about 0.05 and about 1.0% for example, about 0.7% active agent, for example, Everolimus; and
(c) the balance, DMAC solvent.

In the second step of the procedure, which is performed following the drying of the drug-polymer layer of step 1, a topcoat can be applied over the drug-polymer layer.

Step 2: the topcoat can be based on a formulation comprising:
(a) between about 0.1 and about 15%, for example, about 1.5% block copolymer such as Elasteon® copolymer; and
(b) the balance, DMAC solvent.

The block-copolymer can have an average molecular weight within a range of between about 8,000 and about 50,000, for example, about 25,000. Alternative solvents include DMFA, THF, or DMSO.

EXAMPLE 9

A coating can be formed on a stent according to a three-step procedure. The first and the second steps are the same as the steps described in Example 8. In the third step of the procedure, which is performed following the drying of the topcoat layer, a finishing coat is applied over the topcoat. The finishing coat can be based on a formulation comprising between about 0.1 and about 15%, for example, about 2.0% PBT-PEG block copolymer described in Example 4, and the balance, DMAC solvent.

EXAMPLE 10

A coating can be formed on a stent according to a three-step procedure:

Step 1: a coating is applied on the device to form a drug-polymer layer. The coating is made from the following composition:
(a) between about 0.1 and about 15%, for example, about 2.0% EVAL;
(b) between about 0.05 and about 1.0%, for example about 0.7% active agent, for example, Estradiol; and
(c) the balance, DMAC solvent.

In the second step of the procedure, which is performed following the drying of the drug-polymer layer, a topcoat can be applied over the drug-polymer layer.

Step 2: the topcoat can be based on a formulation comprising:
(a) between about 0.1 and about 15%, for example, about 1.8% block copolymer such as Kraton® G-1650 copolymer; and
(b) the balance, THF solvent.

Kraton® G-1650, manufactured by Shell Chemicals Co. of Houston, Tex., is a three block copolymer with hard polystyrene end blocks and a thermoplastic elastomeric poly(ethylene-butylene) soft middle block. Kraton® G-1650 contains about 30 mass % of polystyrene blocks.

In the third step of the procedure, which is performed following the drying of the topcoat layer, a finishing coat can be applied over the topcoat.

Step 3: the finishing coat can be based on a formulation comprising:
(a) between about 0.1 and about 15%, for example, about 2.0% of PBT-PEG block copolymer described in Examples 4 and 9; and
(b) the balance, DMAC solvent.

EXAMPLE 11

A coating can be formed on a stent according to a two-step procedure:

Step 1: a coating is applied on the device to form a drug-polymer layer. The coating can be made from the following composition:
(a) between about 0.1 and about 15%, for example, about 2.0% Elasteon® block-copolymer;
(b) between about 0.05 and about 1.0%, for example, about 0.7% active agent, for example Everolimus; and
(c) the balance, DMAC solvent.

The Elasteon® block-copolymer has the average molecular weight within a range of between about 8,000 and about 50,000, for example, about 25,000. Alternative solvents include DMFA, THF, or DMSO.

In the second step of the procedure, which is performed following the drying of the drug-polymer layer, a topcoat layer is applied over the drug-polymer layer.

Step 2: the topcoat layer can be based on a formulation comprising:
(a) between about 0.1 and about 15%, for example, about 1.5% poly(butyl methacrylate) (PBMA); and
(b) the balance, DMAC solvent.

EXAMPLE 12

The composition can be made according to the formulation described in Example 11, except that instead of PBMA, a copolymer of vinylidene fluoride and hexafluoropropene, poly(vinylidene fluoride-co-hexafluoropropene) (PVDF-HFP) can be used as a topcoat polymer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device comprising a polymer substance wherein the polymer substance comprises a block copolymer comprising a plurality of blocks,
   wherein at least one block comprises:
      a polyisocyanate-derived moiety;
      a polyester-derived moiety, or
      a moiety derived from a copolymer of polyester and polyglycols; and
   wherein at least one other block comprises a hydroxyl-group-containing moiety.

2. The coating of claim 1, wherein the medical device is a stent.

3. The coating of claim 1, wherein the coating additionally includes an active agent.

4. The coating of claim 1, wherein the medical device is a stent and the coating additionally includes an active agent for the treatment of vascular restenosis.

5. The coating of claim 1, wherein the polyisocyanate-derived moiety comprises the reaction product of an isocyanate-derived compound and a hydroxyl-group containing compound.

6. The coating of claim 5, wherein the isocyanate-derived compound comprises a product of a reaction of a diisocyanate with a diol.

7. The coating of claim 6, wherein the diol is 1,4-butanediol.

8. The coating of claim 6, wherein the diisocyanate comprises aliphatic or aromatic diisocyanates.

9. The coating of claim 8, wherein the aliphatic or aromatic diisocyanates are selected from a group consisting of hexamethylene-1,6-diisocyanate and 4,4'-methylene-bisphenyl-diisocyanate.

10. The coating of claim 5, wherein the hydroxyl-group containing compound comprises a polyglycol or a polysiloxane.

11. The coating of claim 10, wherein the polysiloxane is poly(dimethylsiloxane).

12. The coating of claim 10, wherein the polyglycol comprises a poly(alkylene glycol).

13. The coating of claim 12, wherein the poly(alkylene glycol) is poly(ethylene glycol).

14. The coating of claim 1, wherein at least one block comprises a moiety derived from a copolymer of polyester and polyglycols.

15. The coating of claim 14, wherein the polyester comprises a poly(alkylene terephthalate) or poly(L-lactic acid).

16. The coating of claim 15, wherein the poly(alkylene terephthalate) is poly(ethylene terephthalate) or poly(butylene terephthalate).

17. The coating of claim 14, wherein the polyglycol comprises a poly(alkylene glycol).

18. The coating of claim 17, wherein the poly(alkylene glycol) is poly(ethylene glycol).

19. The coating of claim 1, wherein the block copolymer is hexamethylenediisocyanate-butane diol-co-poly(dimethylsiloxane) block copolymer and wherein the polymer substance further includes a polymer selected from poly(butyl-methacrylate) and poly(vinylidene fluoride-co-hexafluoropropene).

20. A composition for coating a medical device, comprising the coating substance of claim 1 and an organic solvent.

21. The composition of claim 20, wherein the organic solvent is selected from a group consisting of dimethylacetamide, trifluoro acetic anhydride, tetrahydrofuran, and 1,2,2-trichloroethylene.

22. A method of fabricating of a medical article, comprising coating an implantable medical device with a polymer substance, wherein the polymer substance comprises a block copolymer comprising a plurality of blocks
   wherein at least one block comprises:
      a polyisocyanate-derived moiety;
      a polyester-derived moiety, or
      a moiety derived from a copolymer of polyester and poly glycols; and
   wherein at least one other block comprises a hydroxyl-group-containing moiety.

23. The method of claim 22, wherein the medical device is a stent.

24. The method of claim 22, wherein the coating additionally comprises a therapeutic substance.

25. The method of claim 22, wherein the medical device is a stent and the coating additionally comprises a therapeutic substance for the treatment of restenosis.

26. The method of claim 22, wherein the polyisocyanate-derived moiety comprises the reaction product of an isocyanate-derived compound and a hydroxyl-group containing compound.

27. The method as claimed in claim 26, wherein the isocyanate-derived compound comprises a product of a reaction of a diisocyanate with a diol.

28. The method of claim 27, wherein the diisocyanate comprises aliphatic or aromatic diisocyanates.

29. The method of claim 28, wherein the aliphatic or aromatic diisocyanates are selected from a group consisting of hexamethylene-1,6-diisocyanate or 4,4'-methylene-bisphenyl-diisocyanate.

30. The method of claim 27, wherein the diol is 1,4-butanediol.

31. The method of claim 26, wherein the hydroxyl-group containing compound comprises a polyglycol or a polysiloxane.

32. The method of claim 31, wherein the polyglycol comprises a poly(alkylene glycol).

33. The method of claim 32, wherein the poly(alkylene glycol) is poly(ethylene glycol).

34. The method of claim 31, wherein the polysiloxane is poly(dimethylsiloxane).

35. The method of claim 22, wherein at least one block comprises a moiety derived from a copolymer of polyester and poly glycols.

36. The method of claim 35, wherein the polyester comprises a poly(alkylene terephthalate) or poly(L-lactic acid).

37. The method of claim 36, wherein the poly(alkylene terephthalate) is poly(ethylene terephthalate) or poly(butylene terephthalate).

38. The method of claim 35, wherein the polyglycol comprises a poly(alkylene glycol).

39. The method of claim 38, wherein the poly(alkylene glycol) is poly(ethylene glycol).

40. The method of claim 22, wherein the block copolymer is hexamethylenediisocyanate-butane diol-co-poly(dimethylsiloxane) block copolymer, and wherein the polymer substance further includes a polymer selected from poly(butylmethacrylate) and poly(vinylidene hexafluoro-co-hexafluoropropene).

* * * * *